US007226934B1

(12) United States Patent
Aberg et al.

(10) Patent No.: US 7,226,934 B1
(45) Date of Patent: Jun. 5, 2007

(54) OPTICALLY ACTIVE ISOMERS OF KETOTIFEN AND THERAPEUTICALLY ACTIVE METABOLITES THEREOF

(75) Inventors: A. K. Gunnar Aberg, Sarasota, FL (US); George E. Wright, Worcester, MA (US); Jan L. Chen, Shrewsbury, MA (US); Andrew T. Maioli, Worcester, MA (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 10/069,663

(22) PCT Filed: Sep. 12, 2000

(86) PCT No.: PCT/US00/24892

§ 371 (c)(1),
(2), (4) Date: Feb. 27, 2002

(87) PCT Pub. No.: WO01/19367

PCT Pub. Date: Mar. 22, 2001

(51) Int. Cl.
*A61K 31/445* (2006.01)
*C07D 409/04* (2006.01)

(52) U.S. Cl. ...................... 514/324; 546/202
(58) Field of Classification Search .............. 514/324; 546/202
See application file for complete search history.

(56) References Cited

U.S. PATENT DOCUMENTS

| | | | | |
|---|---|---|---|---|
| 3,682,930 | A | 8/1972 | Bourquin et al. | 260/293.57 |
| 3,862,156 | A | 1/1975 | Bourquin et al. | 260/293.57 |
| 4,073,915 | A | 2/1978 | Martin | 424/267 |
| 4,128,549 | A | 12/1978 | Bourquin et al. | 546/202 |
| 6,207,684 | B1 * | 3/2001 | Aberg | 514/324 |

FOREIGN PATENT DOCUMENTS

| | | |
|---|---|---|
| CS | 263 993 | 9/1988 |
| EP | 0 339 978 | 11/1989 |
| FR | 1.441.486 | 11/1966 |
| FR | 1.447.527 | 11/1966 |
| WO | 98/43640 | 10/1998 |
| WO | WO 98/56381 | * 12/1998 |

OTHER PUBLICATIONS

The Merck Manual. Eleven Edition. p. 1266.*
Polivka et al. "4H-benzo . . . " CA 112:216595 (1990).*
Cundy et al. "Evidence of stereospecificity in the invivo . . . " EMBASE 1985022681 (1985).*
Bourgeois et al. "Pharmacokinetics of R-enantimeric . . . " EMBASE 1986195020 (1986).*
Boos et al. "Urinary excretion of the enantiomers . . . " EMBASE 19913160244 (1991).*
Garattini "Active drug metabolites . . . " Clin. Pharmacokinetics vol. 10, p. 216-227 (1985).*
Jamali et al. "Bi-directional chiral inversion . . . " Chirality v. 9, p. 29-31 (1997).*
Chen et al. "Determination of ketotifen . . . " Rapid Commun. Mass spectrum v. 17, p. 2459-2463 (2003).*
Waldvogel et al.; "Untersuchungen uber synthetishce Arzneimittle." Helv. Chim. Acta, 1976, 59: 866-877.
Kennedy, G.R.: "Metabolism and pharmacokinetics of ketotifen in children" Research and Clinical Forums, 1982, 4: 17-29.
Julien-Larose C. et al.; "Quantification of Ketotifen and its metabolites in human plasma by gas chromatography mass spectrometry" Biomed Mass Spectrom. 1983, 10: 136-139.
Le Bigot et al.: "Metabolism of ketotifen by human liver microsomes. In vitro characterization of a tertiary amine glucuronidation." Drug Metab. Dispos. 1983, 11: 585-589.
Le Bigot et al.: "Species differences in metabolism of ketotifen in rat, rabbit and man." Life Sci., 1987, 40: 883-890.
Polivka Z. et al.: "4H-benzo(4,5) cyclohepta(1,2-b)thiophenes and 9,10-dihydro derivatives-sulfonium analogues of pizotifen and ketotifen; chirality of ketotifen; synthesis of the 2-bromo derivative of ketotifen." Collect. Czech. Chem. Commun. 1989, 54: 2443-2469.
Mey, U. et al.; "Conjugation of the enantiomers of ketotifen to four isomeric quaternary ammonium glucuronides in humans in vivo and in liver microsomes." Drug Metab Dispos 1999, 27: 1281-1292.
Mey, U et al.; "Enantioselective N-glucuronidation of ketotifen in humans in vitro and in vivo"; Naunyn-Schmiedeberg's Arch Pharmacol 1999, 359:135 (Abstract).
Breyer-Pfaff, U. et al.: "Stereoselective high-affinity reduction of ketonic nortriptyline metabolites and of ketotifen by aldo-keto reductases from human liver."; Adv Exp Med Biol. 1999, 463: 473-480.
Breyer-Pfaff, U. et al.: High-affinity stereoselective reduction of the enantiomers of ketotifen and of ketonic nortriptyline metabolites by aldo-keto reductases from human liver Biochem Pharmacol 2000, 59: 249-260.
Database CAS on STN, (Columbus, OH,USA) AN 113:40470 CA, Polivka et al. 'process for preparing pure enantiomers of 4-(1-methyl-4-piperidylidene-4,9-dihydrobenzo[4,5]cyclohepta[1,2-b]thiophen-10-one as antihistaminics and antianaphylactics'., 1989.
Database CAS on STN, (Columbus, OH,USA) AN 112:216595 CA. Polivka et al. '4H-benzo[4,5-cyclohepta]1,2-bthiophenes and 9,10-dihydro derivatives. Sulfonium analogs of pizotifen and ketoeifen. Chirality of ketotifen. Synthesis of the 2-bromo derivative of ketorifen'. Coll. Czech. Chem. Commun. 91989) vol. 54(9), pp. 2443-2469.
Kofler et al. Experimental chemistry —organic chemistry and reaction. Japan Chemical Society. 1957, vol. 1, pp. 504-505. (Japanese).

(Continued)

*Primary Examiner*—Celia Chang
(74) *Attorney, Agent, or Firm*—Nields & Lemack

(57) ABSTRACT

Racemic norketotifen, racemic 10-hydroxy-ketotifen, racemic 10-hydroxy-nor-ketotifen and optically active isomers of ketotifen, norketotifen, 10-hydroxy-ketotifen and 10-hydroxy-norketotifen were found to have antiallergic and anti-inflammatory effects while being devoid of the severe dose-limiting sedative side effects of ketotifen.

13 Claims, No Drawings

OTHER PUBLICATIONS

Database CAPLUS on STN, (Columbus, OH,USA) AN 1999:793640. Breyer-Pfaff et al. 'High-affinity stereoselective reduction of the enantiomers of ketotifen and of ketonic nortriptyline metabolites by aldo-keto reductases' Biochem. Pharmacol. 1999 vol. 59(3), pp. 240-260.

Helvetica Chimica Acta-vol.59, (1976)- pp. 866-877; Erwin Waldvogel et al. "Untersuchungen über synthetische Arzneimittel 9- und 10-Oxo-derivate von 9, 10-Dihydro-4H-benzol[4,5]cyclohepta[1,2-b]thiophenen".

* cited by examiner

OPTICALLY ACTIVE ISOMERS OF KETOTIFEN AND THERAPEUTICALLY ACTIVE METABOLITES THEREOF

This application is a §371 of PCT/US00/24892 filed Sep. 12, 2000.

TECHNICAL FIELD

This invention relates to methods of treatment of inflammatory and allergic diseases by using nor-ketotifen, 10-hydroxy-ketotifen, 10-hydroxy-norketotifen, or optically active isomers of ketotifen, norketotifen, 10-hydroxy-ketotifen or 10-hydroxy-norketotifen, and pharmaceutically acceptable salts and solvates thereof. More particularly, this invention relates to methods of treating pulmonary diseases (such as asthma, bronchitis) and skin disorders (such as urticaria and atopic dermatitis), and gastro-intestinal disorders (such gastric irritation and enteritis), while avoiding sedative and cardiovascular side effects that are commonly associated with antihistamines. In another embodiment, nor-ketotifen and the optically active isomers of nor-ketotifen were found to be particularly useful for the treatment of ocular diseases such as conjunctivitis and keratitis.

BACKGROUND OF THE INVENTION

This invention relates specifically to anti-inflammatory and antiallergic compounds, having therapeutic use in various diseases, most importantly for patients suffering from pulmonary diseases, including asthma and bronchitis, from dermal diseases, including urticaria and atopic dermatitis and from gastro-intestinal disorders including gastric irritation and enteritis.

The compounds described in this invention are metabolites of ketotifen (4-(1-methyl-4-piperidyline)-4H-benzo(4, 5) cyclohepta-(1,2-b)thiophene-10-one). Due to serious sedative side effects that are related to ketotifen, that compound has limited therapeutic usefulness.

Ketotifen is metabolized in the body along various pathways:

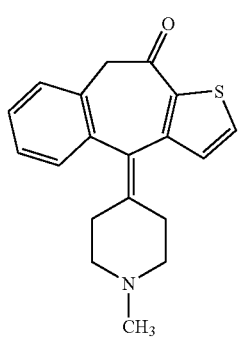

The metabolite norketotifen (also called nor-ketotifen) is formed by demethylation of ketotifen:

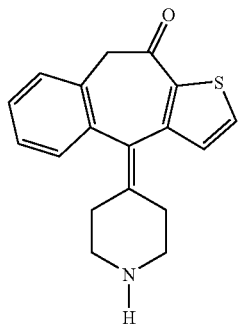

The metabolites 10-hydroxy-ketotifen and 10-hydroxy-norketotifen are formed by reduction of the ketotifen and norketotifen molecules, respectively.

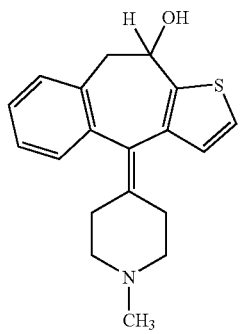

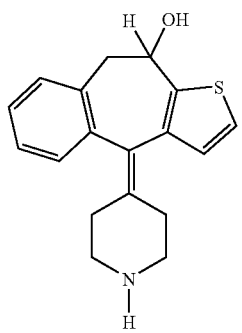

Other metabolites of ketotifen are also formed in the body after administration of ketotifen. Thus, the ketotifen molecule can undergo N-glucuronidation and be converted into N-oxide ketotifen. The hydroxylated isomers can be further metabolized to 10-hydroxy-glucuronidates. Other metabolites may be formed as well and the metabolic pathways are different in various species and may also be different between infants and adults.

No published pharmacological studies of the racemates or the isomers of norketotifen, 10-hydroxy-ketotifen or 10-hydroxy-norketotifen are known to us. Pharmacological properties of the isomers of ketotifen have been described by Polivka et al.: 4H-benzo(4,5)cyclohepta(1,2-b)thiophenes and 9,10-dihydro derivatives-sulfonium analogues of pizotifen and ketotifen; chirality of ketotifen; synthesis of the 2-bromo derivative of ketotifen. Collect. Czech. Chem. Commun. 1989, 54, 2443-2469.

SUMMARY OF THE INVENTION

The isomers of ketotifen have now been synthesized and studied pharmacologically in vitro and in vivo. Various metabolites of ketotifen have also been synthesized and studied pharmacologically. It has been found that the antihistaminic effects of racemic norketotifen are qualitatively similar to the antihistaminic effects of racemic ketotifen. Thus both ketotifen and nor-ketotifen are histamine H-1 antagonists with varying degree of histamine H-2 antagonism. However, surprisingly and importantly, a significant qualitative difference was found between racemic ketotifen and the compounds described in this invention: the compounds described here do not have the severe and dose-limiting sedative activity of ketotifen. It has now also been established that racemic norketotifen and particularly the S isomer thereof has potent anti-inflammatory and anti-histaminic properties with little or no sedative side effect. Likewise, it was found that while both isomers of ketotifen had approximately the same antihistaminic activity, almost all the sedative side effects were found to reside in R(+)-ketotifen. The metabolites 10-hydroxy-norketotifen and 10-hydroxy-ketotifen and the isomers of both compounds were also found to inhibit inflammation and to block histamine H-1 receptors, while causing significantly less sedation than ketotifen.

DETAILED DESCRIPTION

Chemical Syntheses of Ketotifen, Norketotifen, 10-hydroxy-ketotifen and 10-hydroxy-norketotifen, Stereochemically Isomeric Forms and Diastereomers Thereof Racemic ketotifen and norketotifen are made by the methods described in Waldvogel et al. (Helv. Chim. Acta 59, 866-877, 1976) which is hereby incorporated by reference. R-(+)-ketotifen and S-(−)-ketotifen are prepared by fractional crystallization of the salts of racemic ketotifen with (−)-O,O'-di(p-toluyl)-R-tartaric acid and (+)-O,O'-di(p-toluyl)-S-tartaric acid, respectively, as described by Polivka et al. (Collect. Czech. Chem. Commun. 54, 2443-2469, 1989) which is hereby incorporated by reference.

The preferred method for preparation of the optically active isomers of norketotifen, 10-hydroxyketotifen and 10-hydroxy-norketotifen is from the individual R and S enantiomers of ketotifen. A new method of norketotifen synthesis is claimed which avoids the strenuous conditions of Waldvogel et al., 1976) that would result in racemization of the product. Other methods include stereoselective synthesis using chiral templates, resolution of the corresponding racemates using conventional means such as fractional crystallization of diastereomeric salts with chiral acids and chromatography using chiral supports.

The 10-hydroxy derivatives are prepared by catalytic reduction of the corresponding ketotifen enantiomers by methods described by Waldvogel et al., 1976. It must be noted that the 10-hydroxy-ketotifens possess an additional chiral center, and that diastereomers of the corresponding R and S enantiomers of the ketotifens are obtained. These may be separated by conventional crystallization or chromatographic methods because of the differences in solubilities and chromatographic mobilities of diastereomeric isomers. Alternatively, reduction of the R and S enantiomers of the ketotifens with chiral reducing agents may be employed to prepare exclusively (or to greatly enrich mixtures in) the desired diastereomeric product.

Designation of Absolute Configurations.

The enantiomers of ketotifen and norketotifen do not possess asymmetric carbon atoms as is typical of optical isomers. Rather, the enantiomers result from molecular asymmetry due to hindered interconversion of the seven-membered ring. The (+)-ketotifen is designated R and has the configuration observed in the x-ray crystal structure of (+)-ketotifen (−)-O,O'-di(p-toluyl)-R-tartrate by Polivka et al., 1989. (−)-Ketotifen has the S designation.

In the 10-hydroxy ketotifen derivatives, an additional chiral center—the 10-carbon atom—is present, and both R and S configurations exist as defined in standard rules of stereochemistry. In the naming of the diastereomers resulting from reduction of the ketotifen enantiomers, the first letter R or S refers to the configuration of the seven membered ring and the second letter R or S to the configuration of the 10 carbon atom.

Synthesis of (R) and (S)-Norketotifen and of (R) and (S)-Norketotifen Fumarates (These syntheses are summarized in the Scheme.)

(R)-4-(1-(2,2,2-Trichloroethoxycarbonyl)-4-piperidylidene)-9,10-dihydro-4H-benzo-(4,5)-cyclohepta(1,2-b)thiophene-10-one: Anhydrous sodium carbonate (95.0 mg, 898 µmol), (+)-(R)-ketotifen (278 mg, 898 µmol), and benzyltriethylammonium chloride (BTEAC) (205 mg, 898 µmol) were combined in a dry flask and placed under high vacuum for two days. Freshly distilled dichloromethane (2 mL) was then added to the mixture under $N_2$ at room temperature with stirring, followed by the addition of 2,2,2-trichloroethyl chloroformate (556 µL, 4.04 mmol). The biphasic reaction mixture was refluxed for one hour, and after cooling to room temperature, it was quenched by the addition of saturated aqueous sodium carbonate (7 mL). The resulting mixture was diluted with dichloromethane (50 mL), and the organic phase was separated, dried over sodium sulfate, filtered, evaporated and chromatographed ($SiO_2$, ethyl acetate-petroleum ether 20:1 to 10:1). The fractions corresponding to the trichloroethyl carbamate intermediate were pooled, evaporated, and placed under high vacuum resulting in 279 mg, 66% of title compound: $^1$H-NMR (400 MHz, $CDCl_3$) δ 7.58 (s, 1H), 7.37-7.30 (m, 1H), 7.23-7.19 (m, 2H), 7.18-7.11 (m, 1H), 7.03-7.00 (m, 1H), 4.88-4.69 (m, 2H), 4.20 (d, 1H, J=13.0 Hz), 4.03-3.84 (m, 2H), 3.78 (d, 1H, J=13.0 Hz), 3.35-3.09 (m, 2H), 2.75-2.64 (m, 1H), 2.62-2.57 (M, 1H), 2.50-2.39 (m, 2H).

(R)-4-(4-piperidylidene)-9,10-dihydro-4H-benzo-(4,5)-cyclohepta(1,2-b)thiophene-10-one ((R)-Norketotifen): Cadmium dust (178 mg, 1.59 mmol) and a 10% cadmium/lead couple (356 mg, 3.174 mmol) were added to a rapidly stirring mixture of trichloroethyl carbamate (279 mg, 592 µmol) in THF (5.5 mL) and aqueous ammonium acetate (1 M, 3.0 mL) under nitrogen. After 2 hours, the mixture was filtered over celite and washed with copious dichloromethane and water. The filtrate was basified with saturated aqueous sodium carbonate, and the organic layer was separated, dried over sodium sulfate, filtered, and evaporated to give crude (R)-norketotifen (157 mg, 90%). $^1$H-NMR (400 MHz, $CDCl_3$) δ 7.54 (d, 1H, J=5.2 Hz), 7.34-7.29 (m, 1H), 7.23-7.13 (m, 3H), 7.02 (d, 1H, J=5.2 Hz), 4.20 (d, 1H, J=13.6 Hz), 3.76 (m, 1H, J=13.6 Hz), 3.21-3.14 (m, 1H), 3.13-3.05 (m, 1H), 2.86-2.76 (m, 1H), 2.75-2.58 (m, 3H), 2.47-2.39 (m, 2H). Enantiomeric purity was measured by analytical chiral HPLC (Merck Chiradex 5 µm, mobile phase 95:5 pH 4.0 sodium phosphate-acetonitrile, flow rate 1 mL/min, chart speed 0.3 cm/min, 254 nm): $R_t$ 13.0 min, 95% ee.

SCHEME

Synthesis of (R)-NorketotifenFumarate from (+)-(R)-Ketotifen

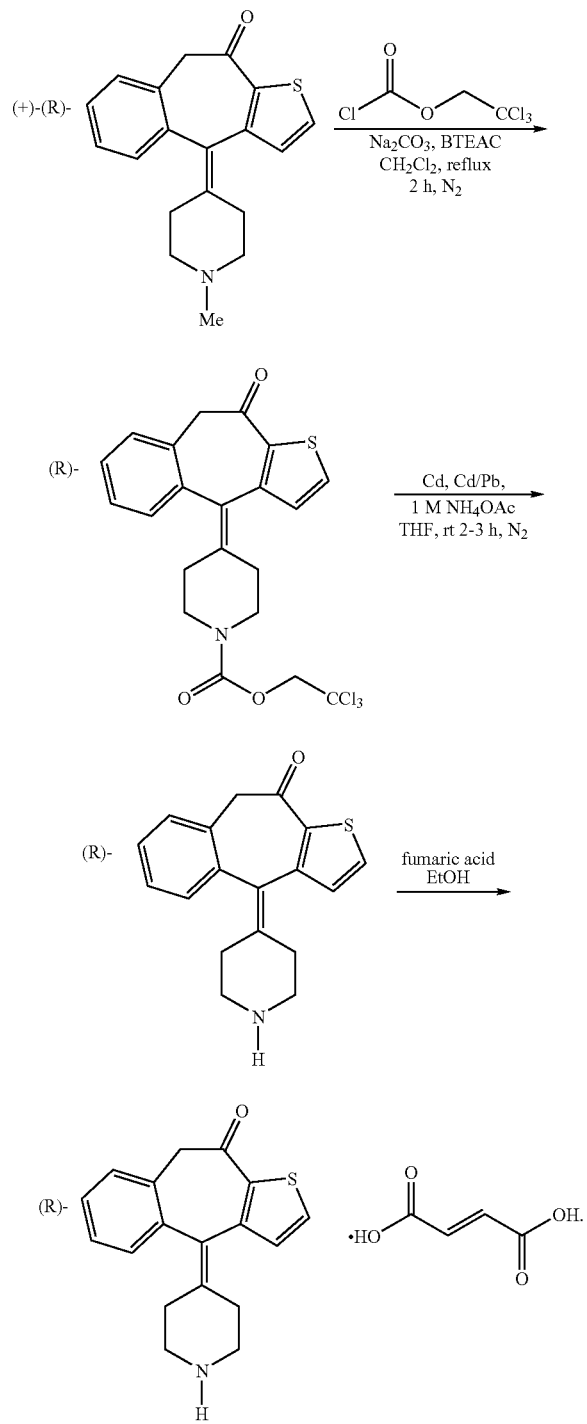

-continued

Synthesis of (S)-NorketotifenFumarate from (-)-(S)-Ketotifen

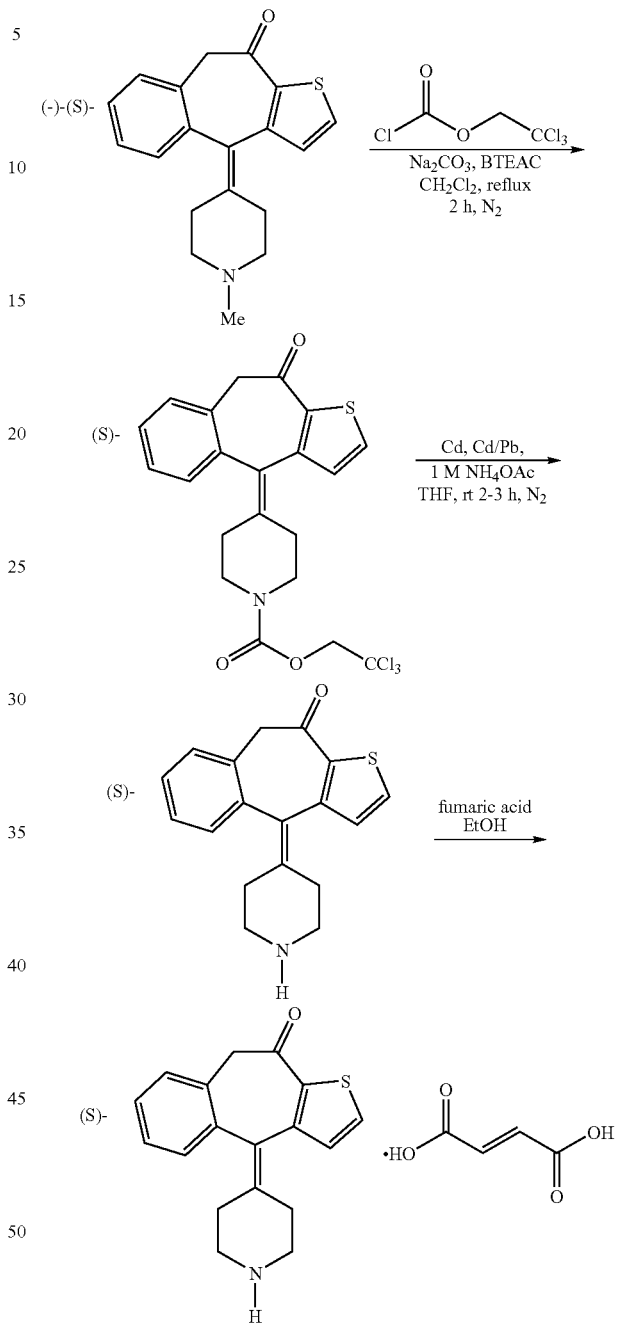

(R)-Norketotifen fumarate: The crude (R)-norketotifen (157 mg, 533 µmol) was taken up in dichloromethane (1 mL) and added to a solution of fumaric acid (61.8 mg, 533 µmol) in ethanol (2 mL). After 50% evaporation of the solvent, crystals of (R)-norketotifen fumarate were collected and washed with ethanol to give 117 mg of product, 57%, after drying under high vacuum: $^1$H-NMR (DMSO-$d_6$) δ 7.99 (m, 1H), 7.40-7.31 (m, 1H), 7.30-7.11 (m, 4H), 6.43 (s, 2H) 4.35 (d, 1H, J=13.2 Hz), 3.65 (d, 1H, J=13.2 Hz), 3.25-3.08 (m, 2H), 2.99-2.89 (m, 1H), 2.83-2.74 (m, 1H), 2.70-2.54 (m, 2H), 2.50-2.40 (m, 1H), 2.38-2.28 (m, 1H). Enantiomeric purity was measured by analytical chiral HPLC (Merck Chiradex 5 μm, mobile phase 95:5 pH 4.0 sodium phosphate-acetonitrile, flow rate 1 mL/min, chart speed 0.3 cm/min, 254 nm): $R_t$ 13.0 min, 95% ee.

(S)-4-(1-(2,2,2-Trichloroethoxycarbonyl)-4-piperidylidene)-9,10-dihydro-4H-benzo-(4,5)-cyclohepta(1,2-b)thiophene-10-one: Following the procedure outlined above for the (R)-enantiomer gave the (S)-enantiomer in similar yields: $^1$H-NMR (400 MHz, CDCl$_3$) δ 7.58 (s, 1H), 7.37-7.30 (m, 1H), 7.23-7.19 (m, 2H), 7.18-7.11 (m, 1H), 7.03-7.00 (m, 1H), 4.88-4.69 (m, 2H), 4.20 (d, 1H, J=13.0 Hz), 4.03-3.84 (m, 2H), 3.78 (d, 1H, J=13.0 Hz), 3.35-3.09 (m, 2H), 2.75-2.64 (m, 1H), 2.62-2.57 (M, 1H), 2.50-2.39 (m, 2H).

(S)-4-(4-piperidylidene)-9,10-dihydro-4H-benzo-(4,5)-cyclohepta(1,2-b)thiophene-10-one: Following the procedure outlined above for obtaining the (R)-enantiomer gave the (S)-enantiomer in similar yields: $^1$H-NMR (400 MHz, CDCl$_3$) δ 7.54 (d, 1H, J=5.2 Hz), 7.34-7.29 (m, 1H), 7.23-7.13 (m, 3H), 7.02 (d, 1H, J=5.2 Hz), 4.20 (d, 1H, J=13.6 Hz), 3.76 (m, 1H, J=13.6 Hz), 3.21-3.14 (m, 1H), 3.13-3.05 (m, 1H), 2.86-2.76 (m, 1H), 2.75-2.58 (m, 3H), 2.47-2.39 (m, 2H). Enantiomeric purity was measured by analytical chiral HPLC (Merck Chiradex 5 μm, mobile phase 95:5 pH 4.0 sodium phosphate-acetonitrile, flow rate 1 mL/min, chart speed 0.3 cm/min, 254 nm): $R_t$ 7.5 min, 95% ee.

(S)-Norketotifen fumarate: Following the procedure outlined above for obtaining the (R)-enantiomer gave the (S)-enantiomer in similar yields: $^1$H-NMR (400 MHz, DMSO-d$_6$) δ 7.99 (m, 1H), 7.40-7.31 (m, 1H), 7.30-7.11 (m, 4H), 6.43 (s, 2H) 4.35 (d, 1H, J=13.2 Hz), 3.65 (d, 1H, J=13.2 Hz), 3.25-3.08 (m, 2H), 2.99-2.89 (m, 1H), 2.83-2.74 (m, 1H), 2.70-2.54 (m, 2H), 2.50-2.40 (m, 1H), 2.38-2.28 (m, 1H). Enantiomeric purity was measured by analytical chiral HPLC (Merck Chiradex 5 μm, mobile phase 95:5 pH 4.0 sodium phosphate-acetonitrile, flow rate 1 mL/min, chart speed 0.3 cm/min, 254 nm): $R_t$ 7.5 min, 95% ee.

Pharmacological Studies of Ketotifen, Norketotifen, 10-OH-ketotifen, 10-OH-nor-ketotifen and the Optically Active Isomers Thereof As discussed above, it has now been shown that the S-isomer of ketotifen, and the racemates and isomeric forms of norketotifen, 10-OH-ketotifen and 10-OH-nor-ketotifen have beneficial pharmacological effects, useful in the treatment of diseases, such as for example allergic disorders, pulmonary disorders, cutaneous disorders and gastrointestinal disorders, while not causing the severe sedative side effects of ketotifen. The surprising findings are described in the following examples.

Test Method 1: Binding to Histaminergic Receptors

The affinities of the racemic and isomeric test compounds for the histamine H$_1$-receptor are assessed using the $^3$H-pyrilamine binding assay as described by Dini et al. (Agents and Actions, 1991, 33: 181-184). Briefly, membranes from guinea pig cerebellum are incubated with $^3$H-pyrilamine and varying concentrations of the test compound(s). The specific binding of the radioactive ligand to the receptor is defined as the difference between total binding and nonspecific binding, determined in the presence of an excess of unlabelled ligand. The results are expressed as percentage of specific binding in the presence of compounds. IC$_{50}$ values (concentration required to inhibit 50% of specific binding) and Hill coefficients (nH) are determined by non-linear regression analysis of the competition curves. These parameters are obtained by Hill equation curve fitting using Sigmaplot™ software.

Test Method 2: Antihistaminic Effects In Vitro

Strips of bronchial or other smooth muscle tissues are removed from the body of male guinea pigs weighing 400-600 g. The tissues are suspended in an oxygenated buffer of the composition (mM): NaCl, 133; KCl, 4.7; CaCl$_2$, 2.5; MgSO$_4$, 0.6; NaH$_2$PO$_4$, 1.3; NaHCO$_3$, 16.3; and glucose, 7.7, or in a solution of a similar composition. The solution is maintained at 37.5 C. Contractions are recorded with isometric transducers (Model FT-10) on a Grass polygraph.

In order to assess the viability of each tissue and to serve as a frame of reference, contractions of each strip of tissue are recorded initially in response to exposure to an oxygenated buffer in which the NaCl is replaced by KCl to yield a concentration of 137.7 mM KCl. This is followed by return to the standard oxygenated buffer, and then by exposures to progressively increasing concentrations of histamine, with separate exposures to each concentration only until the peak response has been recorded. Then, leaving one tissue strip untreated, the remaining strips each are exposed for a predetermined time interval to one concentration of an antagonist. Finally, the responses to increasing concentrations of histamine followed by exposure to 137.7 mM KCl are recorded a second time.

Test Method 3: Binding to Muscarinic Receptors

The experiments are carried out on membranes prepared from SF9 cells infected with baculovirus to express human recombinant muscarinic receptor subtypes. After incubation with the test article and the proper radioligand and washing, bound radioactivity is determined with a liquid scintillation counter, using a commercial scintillation cocktail. The specific radioligand binding to each receptor is defined as the difference between total binding and nonspecific binding determined in the presence of an excess of unlabelled ligand. IC$_{50}$ values (concentrations required to inhibit 50% of specific binding) are determined by non linear regression analysis of the competition curves.

Test Method 4: Inhibition of Bronchial Eosinophil Accumulation

Inhibition of eosinophil accumulation in lung is determined in sensitized guinea pigs (400 to 600 grams) following intraperitoneal injection of an allergen such as for example PAF (platelet aggregating factor) or bovine serum albumin. At a predetermined time thereafter, the animals are killed with a barbiturate. The trachea is exposed and cannulated. 6×10 ml aliquots of buffered modified Tyrode's solution (composition: NaHCO$_3$ 11.9, NaCl 136.9, KCl 2.7, Na$_2$HPO$_4$ 0.4, glucose 5.6, EDTA 19.8, gelatin 0.1% w/v; pH 7.4) are introduced successively and aspirated by gentle compression of the lungs. Total fluid recovery normally exceeds 80%. Cell suspensions are concentrated by low speed centrifugation (200 G for 10 min) and the resulting cell pellet is resuspended in 1 ml modified Tyrode's solution. Total cell counts are made by diluting 10 μl of cell suspension in 90 μl of Turk's fluid. Differential cell counts are made from smears fixed in methanol (100%) and stained in Leishman stain. A total of at least 500 cells per smear are counted at 1000 fold magnification, in order to differentiate cell types. Drugs are administered as sustained subcutaneous infusions from an implanted Alza minipump (Alzet 2001 or similar) or by repeated oral or repeated parenteral injections.

Test Method 5: Dermal Antiinflammatory Effects

Dermal antiinflammatory effects are tested using the mouse ear croton oil inflammation method. This test method is based on Tarrida, J. et al., Meth. Find. Exp. Clin. Pharmacol. (1996) 18(4):233-234 and Blazzo, et al., Prostaglandins (1995) 50:161-168. In short, male mice (25-30 g) are treated with 5 ml/kg of a 2 mg/ml solution of each test compound in physiological saline by intraperitoneal injection. Thirty minutes after injection, croton oil (0, 20 µl of 1.0% croton oil in acetone) or acetone (control) is topically applied to both ears of each mouse. Animals are restrained during croton oil or acetone application and then released into a cage. Before and at predetermined time intervals following croton oil or acetone application, groups of animals are anesthetized with halothane and euthanized by cervical dislocation. Ears are removed and weighed. Average ear weight is plotted against time. A total of 4 animals per timepoint are tested for each compound and the vehicle control.

Test Method 6: Studies on Sedative Side Effects.

The physostigmine-induced lethality test is being used in the present studies. This test is a modification of the sedation test technique reported by VILLANI et al., in U.S. Pat. No. 4,659,716. In short, physostigmine (1.9 mg/kg s.c.) produces 90-100% lethality when given to grouped mice with 10 animals in each plastic cage (11 cm×26 cm×13 cm) Mice administered a sedating agent, such as for example a sedative antihistamine prior to physostigmine are protected and survive. In the present study, test compounds are administered orally 60 minutes prior to physostigmine. The numbers of survivors are counted 30 minutes after physostigmine administration.

Pharmaceutical Compositions

The terms "pharmaceutically acceptable salts" or "a pharmaceutically acceptable salt thereof" refer to salts or solvates prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, succinic, sulfuric, tartaric, p-toluenesulfonic, and the like. The hydrogen fumarate is particularly preferred.

The present invention provides pharmaceutical compositions, which comprise one or more compounds of the invention, formulated together with one or more pharmaceutically acceptable carriers. The pharmaceutical compositions may be specially formulated for oral administration, conjunctival instillation, sublingual administration, parenteral administration, transdermal administration, rectal administration, buccal administration, or for topical administration, or for administration by inhalation or insufflation of powder or aerosol.

Pharmaceutical compositions of this invention can be administered to humans and other mammals orally, sublingually, parenterally, cutaneously, transdermally, rectally, buccally, topically, by conjunctival instillation, or as an oral or nasal spray or aerosol. The term "parenteral" administration includes intravenous, intraarterial, intramuscular, intraperitoneal, intracutaneous, subcutaneous or intraarticular injection and infusion. The term "transdermal" includes the use of various devices ("patches" etc.) that can facilitate or modify the transport or absorption of the drug through skin. The term "topical" refers to application of a composition containing a drug on skin or on mucous membranes.

Oral Administration Forms

Pharmaceutical compositions of this invention for oral administration of solid dosage forms include capsules, granules, pills, powders, and tablets. In such solid dosage forms, the active compound may be mixed with one or more pharmaceutically acceptable excipients or carriers (ex. sodium citrate, dicalcium phosphate), fillers or extenders (ex starch, lactose, sucrose, glucose, mannitol, silicic acid), binders (ex. carboxymethylcellulose, alginates, gelatin, polyvinylpyrrolidone, sucrose, acacia), humectants (ex. glycerol), solution retarding agents (ex. paraffin), disintegrating agents (ex. agar-agar, calcium carbonate, starch, alginic acid, silicates, sodium carbonate), absorption accelerators (ex. quaternary ammonium compounds), wetting agents (ex. cetyl alcohol, glycerol monostearate), absorbents (ex. kaolin, bentonite clay), lubricating agents (ex. talk, calcium stearate, magnesium stearate, polyethylene glycols, sodium lauryl sulfate), and/or buffering agents.

Solid forms of capsules, dragees, granules, pills, and tablets can have coatings and/or shells (ex. enteric coatings) known in the art. The compositions may also be designed to release the active ingredient(s) in a certain part of the gastro-intestinal tract or in a controlled release, slow-release or in a delayed-release manner.

The composition may also be designed for lymphatic absorption of the active ingredient(s).

The active compound(s) can also be micro-encapsulated with one or more of the above-mentioned excipients.

Liquid dosage forms for oral administration include pharmaceutically acceptable emulsions, solutions, suspensions, syrups and elixirs. The liquid dosage form may also contain commonly known diluents (ex. water, other solvents, solubilizing agents), emulsifiers (ex. ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.

Besides inert diluents, the oral compositions can also include adjuvants such as wetting, emulsifying, suspending, sweetening, or flavoring agents.

Suspensions may contain one or more suspending agents known in the pharmaceutical formulating art.

Topical Administration Forms

Compositions for topical administration of the compounds of this invention include solutions, suspensions, droplets, sprays, ointments, cremes and powders. Compositions intended for dermal applications may contain penetration promoting and other agents as known to those skilled in the art. Patches, bandages, etc. may also be used for dermal drug application purposes.

In addition to the therapeutically active ingredients, the composition of this invention for topical administration, including various formulations intended for topical ophthalmic administration, may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, ONAMER M and other agents, known to those skilled in the art. Such preservatives, if utilized, will typically be employed in an amount from 0.001% to 1.0% by weight. Examples of suitable agents, which may be utilized to adjust the tonicity or osmolality of the formulations, include sodium chloride, potassium chloride, mannitol, dextrose glycerin and propylene glycol. Such agents, if utilized, will be employed in an amount of 0.1% to 10.0% by weight (wt. %). The compositions are preferably aqueous, and have a pH in the range of 3.5 to 8.0.

As realized by those skilled in the art, compositions may be formulated in various dosage forms suitable for topical ophthalmic delivery, including solutions, suspensions, emulsions, gels, and erodible solid ocular inserts.

Parenteral Administration Forms

Pharmaceutical compositions for parenteral injections include pharmaceutically acceptable sterile aqueous or non-aqueous solutions, dispersions, suspensions, emulsions and sterile powders for reconstitution into sterile injectable solutions or dispersions prior to use. Various aqueous and nonaqueous carriers, diluents solvents and vehicles may be used (ex. water, ethanol, glycerol, glycol), as well as vegetable oils (ex. olive oil), and organic esters (ex ethyl oleate), or mixtures thereof may be used. Fluidity can be maintained by use of coating material such as lecithin, by restricting particle size and by use of surfactants.

The compositions may also contain adjuvants such as preservatives, wetting agents, emulsifying agents, dispersing agents, antibacterial agents, antifungal agents, isotonic agents, and/or absorption-delaying agents. Absorption-prolonging or absorption-slowing effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polylactide-polyglycolide, polyorthoesters, polyanhydrides) or by using various types of liposomes or microemulsions to hold the drug. Formulations for injection can be sterilized by various methods.

Administration by Inhalation

Compounds of the present invention, as for example norketotifen, can be administered by inhalation, which may be a preferred route of administration by certain patients, such as for example patients suffering from asthma. Various inhalation devices, such as for example metered dose inhalers, dry powder inhalers and nebulizers, may be used as known by those skilled in the art.

Rectal Administration Forms

Compositions for rectal administration are preferably suppositories.

Buccal Administration Forms

Compositions for buccal administration are preferably toothpastes, mouthwashes, sublingual preparations, chewing gums etc.

Sublingual Administration Forms

Various galenic formulations can be used: concentrated solutions or suspensions of the drug may be applied sublingually by various drop devices; various aerosol devices may be used to spray the drug onto the oral mucus membranes; specifically designed fast dissolving tablets, capsules or powders may as well be used for fast delivery of the full dose.

Transdermal Administration Forms

Compositions for transdermal administration of the compounds of this invention include various known patches, bandages etc.

Oral (Buccal) or Nasal Spray or Droplet Administration

Compositions for oral or nasal sprays or droplets may be in the form of solutions, suspensions or dry powders and may be designed for nasal, buccal, bronchial/pulmonary, and/or gastric absorption of the drug.

Therapeutic Dose Levels

Since the compounds of the present invention do not express the severe and dose-limiting sedative side effects of ketotifen, the compounds of this invention may be given in higher doses than are presently used for ketotifen.

The actual dosage levels of active ingredients in the pharmaceutical compositions of this invention may be varied so as to obtain the desired therapeutic effect. Thus the amount of drug used varies and may depend on factors such as administration form, severity of the disease, frequency of dosing etc. For use as medication to patients suffering from benign airways or bronchial disorders (such as asthma, bronchitis, etc.), oral doses of the compound of this invention are used at dose levels of 0.5 mg to about 200 mg, preferably from 1 mg to 20 mg once to four times daily to a patient weighing 60 kg. The daily dose may be increased or decreased depending on various factors, for example the weight and the disease status of the patient.

As an example, for use as medication to patients suffering from a seasonal allergic condition, such as for example allergic rhinitis, oral doses of a compound of this invention may be used at dose levels of 0.1 mg to about 100 mg, preferably from 1 mg to 20 mg once to four times daily to a patient weighing 60 kg. For patients suffering from seasonal allergic conjunctivitis, the concentration of a solution containing a compound of this invention for instillation into the conjunctival sac may contain from 0.01% to 4.0%, preferably 0.02% to 2.0% of the active ingredient. For patients suffering from asthma, a compound of this invention is used at an oral dose level of 2 to 100 mg, preferably 2 to 20 mg once to four times daily to a patient weighing 60 kg. The frequency and amount of the dosage will be determined by the clinician based on various clinical factors, such as for example the weight and the severity of the disease of the patient. The ocular use will typically comprise topical application of one to two drops (or an amount of a solid or semisolid dosage form) to the affected eye one to four times per day. The dermal use will typically comprise dermal application of an ointment containing 0.1% to 10.0% of a compound of this invention.

Oral Dosage Formulations

Example of a tablet formulation.

| Ingredients | per tablet | per batch of 10,000 tablets |
|---|---|---|
| Norketotifen | 3 mg | 30 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The active ingredient (in the example above, the compound racemic norketotifen) is blended with lactose and cellulose until a uniform blend is formed. The lake is added and further blended. Finally, the calcium stearate is blended in, and the resulting mixture is compressed into tablets using a ⁹⁄₃₂-inch (7 mm) shallow concave punch. Tablets of other strengths may be prepared by altering the ration of active ingredient to the excipients or to the final weight of the tablet. Formulations intended for oral administration may contain other or additional ingredients than those of this example, as described above under the heading "Oral administration forms."

Therapeutic Indications

The compounds of the present invention may be used for various therapeutic indications, including such indications for which ketotifen may be useful. The compounds of the present invention have pharmacological effects that are similar to those of ketotifen, but the present compounds do not have the severe sedative side effects that are dose-limiting when the parent compound (ketotifen) is used for therapeutic purposes.

This invention provides methods for the treatment and/or prophylaxis of all forms of allergic disorders, including but not limited to allergic rhinitis, multi-system allergies, dermal and ocular allergies. These methods comprise administering to a mammal of a drug of this invention, either as a single isomer or a mixture of isomers or a pharmaceutically acceptable salt or solvate thereof.

This invention also provides methods for the treatment and/or prophylaxis of bronchial and pulmonary disorders, including but not limited to asthma, bronchitis, bronchial hyperreactivity, cough and chronic obstructive pulmonary disease (COPD). These methods comprise administering to a mammal of a drug of this invention, either as a single isomer or a mixture of isomers or a pharmaceutically acceptable salt or solvate thereof.

This invention also provides methods for the treatment and/or prophylaxis of dermal disorders, including but not limited to atopic dermatitis, urticaria, other itching or inflammatory conditions and psoriasis. These methods comprise administering to a mammal of a drug of this invention, either as a single isomer or a mixture of isomers or a pharmaceutically acceptable salt or solvate thereof.

This invention provides methods for treatment and/or prophylaxis of forms of ocular diseases such as conjunctivitis, keratitis, blepharitis, episcleritis, scleritis, anterior uveitis, posterior uveitis, endophthalmitis, optic neuritis, cranial arteritis, sympathetic ophthalmia in mammals, such as humans, while avoiding ocular irritation, sedation and other toxic manifestations of ketotifen and steroids. These methods comprise administering to a mammal of a drug of this invention, either as a single isomer or a mixture of isomers or a pharmaceutically acceptable salt or solvate thereof.

This invention provides methods for treatment and/or prophylaxis of forms of gastroenterological diseases such as for example hyperactivity or hypersecretory syndromes including Zollinger-Ellison syndrome, gastric irritation, enteritis, gastric or duodenal ulcers, acid indigestion, heartburn, motility disorders, gastric reflux or undesired gastric acid secretion. These methods comprise administering to a mammal of a drug of this invention, either as a single isomer or a mixture of isomers or a pharmaceutically acceptable salt or solvate thereof.

Co-Administration

This invention also provides methods for co-administration of one or more compounds of this invention with adrenergic agonists, including but not limited to albuterol, terbutaline, fenoterol, formoterol or salmeterol, thereby eliminating or decreasing side effects that may be induced by said beta-agonist therapy.

The invention also provides methods for co-administration of a compound of this invention with agents or drugs causing bronchial hyperreactivity, including but not limited to adrenergic beta-receptor blocking agents or cyclooxygenase inhibitors, thereby eliminating or decreasing the bronchial hyperreactivity that is induced by such therapy. This invention also provides methods for co-administration of a compound of this invention, with at least one drug of the following classes: ocular antihypertensive agents, adrenergic antagonists, antibacterial agents, antiviral agents, steroids, cyclooxygenase inhibitors, leukotriene antagonists, lipoxygenase inhibitors, local anesthetics and ocular therapeutic remedies. The present invention also provides for co-administration of a compound of this invention with decongestants, such as for example phenylephedrine, naphazoline, tetrahydrozoline or with antibacterial agents, such as bacitracin, neomycin and polymyxin.

EQUIVALENTS

Those skilled in the art will recognize, or be able to ascertain, using no more than routine experimentation, many equivalents to the specific embodiments of the invention described herein. Such equivalents include the therapeutic use of a single isomer and a composition containing same, while avoiding the side effects residing in the corresponding isomer(s) or in the parent compound (ketotifen) or an isomer thereof. Equivalents also include numerous pharmaceutically acceptable salt forms e.g. sulfate, hydrobromide, hydrochloride, dihydrochloride, methanesulphonate, fumarate, hydroxynaphthoate or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4; 2/2) 32. Equivalents also include the co-administration of at least one compound of the present invention with any other drug that is used to combat diseases in mammals, mentioned in this document. Those skilled in the art of medicine may also realize that higher or lower doses than those indicated here may be preferred and the doses may be given more or less frequently than suggested here.

Those skilled in the art of pharmacology, realize that bronchial hyperreactivity is commonly seen in patients suffering from various pulmonary conditions, such as for example asthma. Furthermore, people skilled in the art also realize that bronchial hyperreactivity may be induced by drugs, such as for example adrenergic beta-receptor agonists.

The compounds of the invention, having certain pharmacological properties (such as inhibitory activity on various types of histamine receptors, PAF-antagonistic activity, effects on nitric oxide synthase, mast cell stabilizing activity, etc.) are useful for other indications than those listed here. Such indications are equivalents to the specific embodiments of the invention described herein.

By using a single isomer of a compound of the present invention, it is possible to avoid side effects residing in the corresponding distomer. Such side effects may include for example cardiovascular side effects, such as for example cardiodepression and cardiac arrhythmias, gastrointestinal side effects, such as for example irritation, or CNS side effects, such as for example sedation or drowsiness. All equivalents are intended to be included in this present invention.

The invention claimed is:

1. A pharmaceutical composition comprising an effective amount of the S-isomer of a compound having the structure:

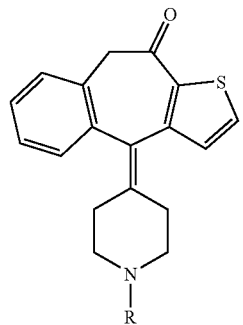

where R is H, and pharmaceutically acceptable salts thereof, together with a pharmaceutically acceptable carrier, said composition being free of sedative side effects and being substantially free of the corresponding R-isomer.

2. A pharmaceutical composition comprising an effective amount of the S-isomer of a compound having the structure:

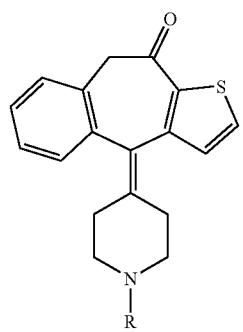

where R is H, and pharmaceutically acceptable salts thereof, together with a pharmaceutically acceptable carrier, wherein said compound has an optical purity of at least 95% ee.

3. A synthetically produced substantially optically pure form of the S-isomer of a compound of the structure:

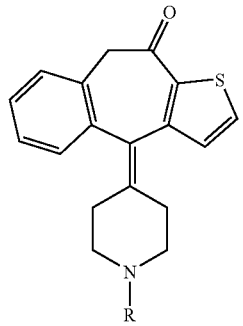

where R is H.

4. A method for synthesis of the stereochemically active compounds of the structure:

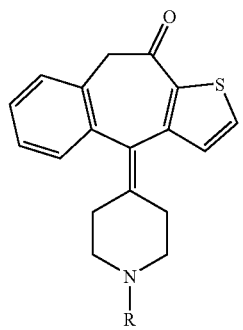

wherein R is H, being of the R- or S-configuration, comprising the conversion of the corresponding stereochemical isomers of ketotifen into their 1-(2,2,2,-trichloro ethoxycarbonyl) nor-intermediates, followed by Cd/Pb-catalyzed cleavage to the final products S-norketotifen or R-norketotifen.

5. A method for treating a disease selected from the group consisting of allergic disorders against which ketotifen has therapeutic activity, dermal disorders against which ketotifen has therapeutic activity, bronchial disorders against which ketotifen has therapeutic activity, pulmonary disorders against which ketotifen has therapeutic activity, and gastroenterological disorders against which ketotifen has therapeutic activity, which comprises administering to a mammal in need thereof a therapeutically effective amount of the S-isomer of norketotifen or a pharmaceutically acceptable salt thereof, substantially free of the corresponding R-isomer, while eliminating the dose-limiting sedative side effects of ketotifen.

6. The method of claim 5, wherein said bronchial or pulmonary disorder is selected from the group consisting of chronic obstructive pulmonary disease (COPD), asthma, cough, bronchitis and bronchial hyperreactivity.

7. The method of claim 5, wherein said allergic disorder is selected from the group consisting of allergic rhinitis and allergic conjunctivitis.

8. The method of claim 5, wherein said dermal disorder is selected from the group consisting of atopic dermatitis, urticaria, and psoriasis.

9. The method of claim 5, wherein the therapeutically active compound or a pharmaceutically acceptable salt thereof is administered by inhalation or by nasal, parenteral, topical, dermal, transdermal, rectal, sublingual, conjunctival or oral administration.

10. The method according to claim 5, wherein the therapeutically active compound or a pharmaceutically acceptable salt thereof is administered orally.

11. The method according to claim 5, wherein the therapeutically active compound or a pharmaceutically acceptable salt thereof is administered orally in an extended release formulation.

12. The method according to claim 5, wherein the amount of the therapeutically active compound is administered from about 0.5 mg to about 200 mg, one to four times per day.

13. The method according to claim 5, wherein a solid, semi-solid, liquid, suspension, aerosol or topical or transdermal pharmaceutical composition, comprising a therapeutically effective amount of the therapeutically active compound, or a pharmaceutically acceptable salt thereof, is administered in combination with a pharmaceutically acceptable carrier or carrier system.

* * * * *

UNITED STATES PATENT AND TRADEMARK OFFICE
CERTIFICATE OF CORRECTION

| | |
|---|---|
| PATENT NO. | : 7,226,934 B1 |
| APPLICATION NO. | : 10/069663 |
| DATED | : June 5, 2007 |
| INVENTOR(S) | : A. K. Gunnar Aberg et al. |

It is certified that error appears in the above-identified patent and that said Letters Patent is hereby corrected as shown below:

Column 1, first paragraph after title, please add the following after "Sep. 12, 2000":

-- , which claims priority of U.S. Provisional Appln. Serial No. 60/153,566 filed September 13, 1999, U.S. Provisional Appln. Serial No. 60/197,363 filed April 15, 2000, U.S. Provisional Appln. Serial No. 60/197,905 filed April 15, 2000, U.S. Provisional Appln. Serial No. 60/197,906 filed April 15, 2000, and U.S. Provisional Appln. Serial No. 60/197,985 filed April 15, 2000. --

Signed and Sealed this

Twenty-fourth Day of March, 2009

JOHN DOLL
*Acting Director of the United States Patent and Trademark Office*